United States Patent
Willbold et al.

(10) Patent No.: US 10,174,097 B2
(45) Date of Patent: Jan. 8, 2019

(54) SPECIFIC A-BETA SPECIES-BINDING PEPTIDES FOR THE THERAPY AND/OR DIAGNOSIS OF ALZHEIMER'S DEMENTIA

(71) Applicant: Forschungszentrum Juelich GmbH, Juelich (DE)

(72) Inventors: Dieter Willbold, Juelich (DE); Janine Kutzsche, Dueren (DE); Antonia Klein, Calgary (CA)

(73) Assignee: Forschungszentrum Juelich GmbH (DE)

( * ) Notice: Subject to any disclaimer, the term of this patent is extended or adjusted under 35 U.S.C. 154(b) by 0 days.

(21) Appl. No.: 15/549,725

(22) PCT Filed: Feb. 25, 2016

(86) PCT No.: PCT/DE2016/000089
§ 371 (c)(1),
(2) Date: Aug. 9, 2017

(87) PCT Pub. No.: WO2016/150415
PCT Pub. Date: Sep. 29, 2016

(65) Prior Publication Data
US 2018/0044398 A1    Feb. 15, 2018

(30) Foreign Application Priority Data

Mar. 20, 2015    (DE) .................. 10 2015 003 676

(51) Int. Cl.
| | | |
|---|---|---|
| C07K 14/705 | (2006.01) | |
| A61K 38/00 | (2006.01) | |
| C07K 14/47 | (2006.01) | |

(52) U.S. Cl.
CPC ........ C07K 14/705 (2013.01); C07K 14/4713 (2013.01); A61K 38/00 (2013.01)

(58) Field of Classification Search
CPC ....... C07K 14/705; A61K 38/04; A61K 38/10
See application file for complete search history.

(56) References Cited

U.S. PATENT DOCUMENTS

| 2007/0093415 A1 | 4/2007 | Martin |
|---|---|---|
| 2015/0284432 A1 | 10/2015 | Willbold et al. |

FOREIGN PATENT DOCUMENTS

| DE | 102012102998 B4 | 12/2013 |
|---|---|---|
| DE | 102012022013 A1 | 5/2014 |
| WO | WO-02081505 A2 | 10/2002 |
| WO | WO-2013150126 A2 | 10/2013 |
| WO | WO-2014041115 A2 | 3/2014 |
| WO | WO-2015043566 A1 | 4/2015 |

OTHER PUBLICATIONS

Translation of WO 02/081505A2 description by Patent Translate, EPO Espacenet, retrieved Jun. 9, 2018. 13 pages. (Year: 2018).*
Translation of WO 02/081505A2 claims by Patent Translate, EPO Espacenet, retrieved Jun. 9, 2018. 4 pages. (Year: 2018).*
Schumacher et al: "Identification of D-Peptide Ligands Through Mirror-Image Phage Display" Science. American Association for the Advancement of Science. US. Bd. 271 Mar. 29, 1996.

* cited by examiner

*Primary Examiner* — Kimberly Ballard
(74) *Attorney, Agent, or Firm* — Jordan and Koda, PLLC (57) ABSTRACT

The invention relates to peptides binding specifically to Abeta species for treating and/or diagnosing Alzheimer's disease.

10 Claims, 7 Drawing Sheets

Specification includes a Sequence Listing.

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: D-Peptide, ANK6

<400> SEQUENCE: 1

Arg Lys Arg Ile Arg Leu Val Thr Lys Lys Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: D-Peptide, ANK7 (with 4-Fluoro-phenylalanine
      (D) at Position 7 instead of Phenylalanine)

<400> SEQUENCE: 2

Arg Lys Arg Val Arg Leu Phe Thr His Ile Lys Arg
1               5                   10

<210> SEQ ID NO 3
<211> LENGTH: 12
<212> TYPE: PRT
<213> ORGANISM: Artificial Sequence
<220> FEATURE:
<223> OTHER INFORMATION: D-Peptide, ANK5

<400> SEQUENCE: 3
```

```
Arg Lys Arg Val Arg Leu Val Tyr His Lys Lys Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: D-Peptide, ANK4

<400> SEQUENCE: 4

Arg Lys Arg Ile Arg Leu Val Tyr His Trp Asn Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: D-Peptide, ANK1

<400> SEQUENCE: 5

Arg Lys Arg Ile Arg Leu Val Tyr His Ile Asn Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: D-Peptide, ANK2 (with Phenylglycine (D) at
      Position 7 instead of Glycine)

<400> SEQUENCE: 6

Arg Lys Arg Ile Arg Leu Gly Tyr His Ile Asn Arg
1               5                   10

<210> SEQ ID NO 7
<211> LENGTH: 12
<212> TYPE: PRT
<213> ORGANISM: Artificial Sequence
<220> FEATURE:
<223> OTHER INFORMATION: D-Peptide, ANK3 (with Phenylglycine (D) at
      Position 7 instead of Glycine)

<400> SEQUENCE: 7

Arg Lys Arg Ile Arg Leu Gly Tyr His Trp Asn Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: D-Peptide, ANK15 (with Phenylglycine (D) at
      Position 7 instead of Glycine)

<400> SEQUENCE: 8

Arg Pro Arg Val Arg Leu Gly Tyr His Trp Asn Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: D-Peptide, ANK16 (with Homoarginine (D) at
```

```
          Position 4 instead of Arginine)

<400> SEQUENCE: 9

Arg Lys Arg Arg Arg Leu Val Thr Lys Arg Asn Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: D-Peptide, ANK17 (with Phenylglycine (D) at
      Position 7 instead of Glycine)

<400> SEQUENCE: 10

Arg Lys Arg Ile Arg Leu Gly Tyr His Ile Lys Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: D-Peptide, ANK18 (with Homoarginine (D) at
      Position 4 instead of Arginine)

<400> SEQUENCE: 11

Arg Pro Arg Arg Arg Leu His Thr Lys Lys Lys Arg
1               5                   10
```

SPECIFIC A-BETA SPECIES-BINDING PEPTIDES FOR THE THERAPY AND/OR DIAGNOSIS OF ALZHEIMER'S DEMENTIA

The invention relates to peptides binding specifically to Abeta species for treating and/or diagnosing Alzheimer's disease.

BACKGROUND OF THE INVENTION

As of yet, no approved drug exists for treating the cause of Alzheimer's Disease (AD). Typically, deposits of the so-called beta amyloid peptides (Aβ) in plaques are found in the brains of AD patients post mortem. This is the reason why, for quite some time, various forms of the Abeta (also referred to as Aβ), such as fibrils, have been considered to be responsible for the development and progression of Alzheimer's disease.

In recent years, in particular the small, freely diffusable Aβ oligomers have been regarded as the primary causative factor in the development and progression of Alzheimer's disease.

Aβ monomers are continuously created in our body and are presumably not toxic per se.

There is speculation as to whether Aβ monomers agglomerate to form Aβ oligomers randomly as a function of the concentration thereof, which ultimately results from formation and decomposition rates in the body, and thus, with increasing age, are increasingly likely to do so spontaneously. Once Aβ oligomers have developed, it is possible that they then multiply by way of a prion-like mechanism and ultimately lead to disease.

Based on these considerations, it should be the goal of a causative treatment to completely destroy toxic Aβ oligomers and/or prevent the prion-like multiplication thereof.

However, no drug for the treatment for Alzheimer's disease is available which acts to combat the cause. Drugs that are used according to the prior art are able to alleviate some symptoms at best, but cannot slow, let alone stop, the progression of the disease.

A number of substances exist that, in animal experiments, are able to achieve some success in terms of prevention (not necessarily the treatment) of Alzheimer's disease.

An important distinction between prevention and treatment lies in the following consideration: So as to prevent the formation of initial Aβ oligomers, Aβ ligands having low affinity and effectiveness may suffice. Since the formation of an Aβ oligomer from multiple Aβ monomers is a reaction of a very high order, it is dependent to a high degree on the Aβ monomer concentration. Even a small reduction in the active Aβ monomer concentration can thus prevent the initial Aβ oligomers from forming. This is the situation with prevention. However, if Aβ oligomers have already been created, these are able to multiply in a prion-like manner, which is not a reaction of a high order and consequently almost independent of the Aβ monomer concentration. This is the situation with treatment. As a result, if Aβ oligomers have already been created, the goal of a treatment must be to address these with substances that have the highest possible affinity to Aβ oligomers. The corresponding dissociation constant would have to be in the pM range, or even lower.

At present, several substances exist that reduce the concentration of Aβ monomers in a wide variety of ways, for example by way of gamma secretase modulators, Aβ-binding ligands, and so forth. This appears to suffice to provide successful preventive action in animal experiments, in which animals are usually already undergoing treatment before the disease fully manifests itself.

In clinical human trials (phases II and III), where only individuals that have been clearly diagnosed with Alzheimer's disease are allowed to be treated, however, all these substances have failed so far, possibly because, in these instances, which is to say prior to the onset of the disease, a small or moderate decrease in the Aβ monomer concentration is not sufficient to prevent the development of increasingly greater amounts of Aβ oligomers.

Furthermore, it is not currently possible to diagnose Alzheimer's disease reliably before symptoms appear. Today, Alzheimer's disease is primarily detected through neuropsychological tests on persons already suffering from symptoms of dementia. Furthermore, other diseases (traumas) can be excluded by way of various examination methods.

However, it is known that Aβ oligomers, and subsequently plaque, develop in the brain of patients up to 20 years prior to the appearance of symptoms and cause irreversible damage. Molecular probes, which are intravenously injected into the patient and bind to Aβ oligomers and plaque after passing the blood-brain barrier, can be rendered visible by way of imaging methods, and thus allow an earlier diagnosis of AD.

A D-enantiomeric peptide by the name "D3" is known from EP 1 379 546 B1. The peptide was identified by way of a mirror image phage display selection against predominantly monomeric Aβ(1-42), with the goal of stabilizing the same with the bond and preventing conversion into toxic Aβ aggregates. Based on current knowledge, D3 preferably converts the particularly toxic Aβ oligomers into non-toxic, non-amyloidogenic and ThT negative amorphous aggregates. In animal models, even oral administration of D3 with drinking water results in treated transgenic AD mice containing considerably less plaque and having significantly improved cognitive abilities.

Further peptides derived from D3 are known from the publication WO 2014/041115 A2.

The disadvantage is that the existing Aβ oligomer-binding substances have insufficient affinity to prevent the multiplication of Aβ oligomers.

A disadvantage is that, so far, there are no probes for in vivo imaging methods which bind with high affinity specifically to Aβ oligomers and render these visible. Since Aβ oligomers play such an important and early role in the history of the disease, precisely this would be desirable.

SUMMARY OF THE INVENTION

It is the object of the invention to provide peptides for the
A) causal treatment of Alzheimer's disease by preventing the formation of toxic amyloid-β (Aβ) oligomers or aggregates or by detoxifying the same,
B) diagnosis of Alzheimer's disease by using the D-peptides as a probe for in vivo imaging.

It was also an object to provide novel peptides, preferably derivatives of the D-enantiomeric D-peptide D3, which have more efficient properties than D3. The properties include, among other things, a binding affinity and specificity for Abeta species, inhibition of Abeta fibril formation, inhibition of Abeta cytotoxicity, elimination or detoxification of Abeta oligomers, fibrils and other aggregates, and conversion of Abeta amyloid fibrils, protofibrils or oligomers into non-toxic, non-amyloidogenic species.

Hereafter, the terms "Abeta," "amyloid beta," "amyloid β" and "Aβ." are used synonymously.

The object of the invention is achieved by the peptides according to claim 1, by the kit and the composition according to the main claims, and by the methods and uses according to the additional independent claims. Advantageous embodiments will be apparent from the respective claims dependent thereon.

This object is achieved by specifically amyloid beta species-binding peptides for treating Alzheimer's disease. Specificity, often also referred to as selectivity, shall be understood to mean that the ligand according to the invention or a peptide according to the invention is essentially able to bind different Abeta species, such as Abeta P4 or Abeta oligomer or Abeta fibrils. Assuming a 1:1 binding model, a respective dissociation constant ($K_D$) or an association constant ($K_A=1/K_D$) is associated with each binding pair (for example, ligand to Abeta monomer, and ligand to Abeta oligomer, and ligand to Abeta fibrils). The higher the $K_A$ value, the higher the affinity of the respective bond.

The specificity of the ligand for the bait as compared to the competitor is expressed by a preferably large quotient of the affinities and the Abeta monomer, and the Abeta oligomer or Abeta fibrils.

According to the invention, quotients of the $K_A$ values of the ligand and the Abeta monomer, and the Abeta oligomer (or Abeta fibrils) are thus used to determine the specificity. The greater the quotient, the higher the specificity.

Within the meaning of the invention, relative specificity refers to the quotient of the $K_A$ values of the ligand and species A, and of the ligand and species B, being at least greater than 1, preferably greater than 1.2 or 1.5, preferably greater than 2, 3, 4, 5, 6, 7, 8, 9, in particular 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and in particular 100, wherein the different Abeta species monomer, oligomer and fibrils can be assumed as species A and species B.

The specificity or selectivity is not to be confused with the affinity that results from the binding strength of ligands to one of the species. When different ligands compete for the same target molecule, a less specific or selective one can have a higher binding affinity. According to the invention, the ligand to be determined is that which binds particularly specifically to a species such as monomer or oligomer or fibrils. The biomolecules are to be suitable as therapeutic agents and remedies. The ligands or peptides thus obtained have the desired properties and achieve the object of the invention.

In particular, the following peptides, serving as ligands, comprising an amino acid sequence according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11 and/or homologs, fragments and parts thereof achieve the object of the invention.

This object is also achieved by polymers comprising an amino acid sequence according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11 and/or the homologs, fragments and parts thereof.

The peptides comprising one of the described sequences specifically bind to the amyloid beta monomer.

Specific binding to Abeta monomer, incidentally, shall be understood to mean that the quotient of the binding signals of the ligand monomer and the ligand oligomer and/or of the ligand monomer and ligand fibrils is greater than 1, such as 1.8, and, for example, can take on a value up to 100, wherein any intermediate value, such as 2, 3, 4, 5, 6, 7, 8, 9, in particular 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and in particular 100, is possible.

Specific binding to Abeta oligomer shall be understood to mean that the quotient of the binding signals of the ligand oligomer and the ligand monomer, or of the ligand oligomer and ligand fibrils, is greater than 1, such as 1.2, and, for example, can take on a value up to 100, wherein any intermediate value, such as 2, 3, 4, 5, 6, 7, 8, 9, in particular 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and in particular 100, is possible.

Rounding of uneven numerical values, which is customary in scientific practice, results in the above-mentioned numerical values.

Peptides obtained by way of peptide microarray experiments, for example, form the starting point. These may be derived from the known peptide "D3."

The procedure for identifying peptides that bind specifically to amyloid beta monomer or specifically to amyloid beta oligomers and for determining the binding specificity of peptides within the meaning of the present invention can thus be as follows. Peptide microarrays comprising various peptides immobilized on a surface, such as derivatives of D3, are each incubated with different species of Abeta (such as monomers, oligomers and fibrils) labeled with a fluorescent dye. A peptide microarray is incubated with only the fluorescent dye to serve as the control. So as to ensure the reproducibility of the results, the incubation of the peptide microarrays can be carried out at least three times for each species. The binding of the fluorescence-labeled Abeta to the immobilized peptides is detected by way of the fluorescent dye. The more Abeta binds to the peptide, the higher the fluorescence signal is. The measured fluorescence signals of the reproductions are standardized, and the signal is subtracted from the control. This avoids binding of the fluorescence-labeled Abeta via the dye. The binding signals of an Abeta species to a peptide are then averaged. So as to determine the binding specificity, the quotient of the species to which the peptide is to specifically bind and another species is found.

Example: binding specificity of peptide X to Abeta monomers=binding signal of peptide X to monomers/binding signal of peptide X to oligomers (or fibrils). Peptides binding specifically to Abeta oligomer are ascertained analogously.

Fragments and parts of the peptides according to the invention exhibit a similar or identical effect as the peptides according to the invention.

In one variant of the invention, peptides are ascertained and used which bind to an Abeta monomer or Abeta oligomer or to Abeta fibrils with a $K_D$ of no more than 500 μM, preferably 250, 100, 50 μM, particularly preferably 25, 10, 6 μM, and in particular 4, 2, 1 μM or sub-ρM.

In one variant, the peptides according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO; 10, and/or SEQ ID NO: 11 and the homologs, fragments and parts are substantially, preferably at least 60%, 75%, 80%, particularly preferably 85%, 90%, 95%, and in particular 96%, 97%, 98%, 99%, 100% composed of D-amino acids.

A polymer within the meaning of the invention is formed of at least 2, or 3, 4, 5, 6, 7, 8, 9, 10, 11, 12, 13, 14, 15, 16, 17, 18, 19, 20 or more monomers or monomer units, selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and/or SEQ ID NO: 11 and/or the homologs, fragments or parts thereof, which on their own already bind to Abeta monomers or Abeta oligomers or Abeta fibrils.

According to the invention, the polymers are composed of identical monomer units, or of a combination of 2, 3, 4, 5, 6, 7, 8, 9, 10 or 11 various different above-mentioned monomers, as so-called combination polymers. Some of the monomers can also be identical. The number of identical monomers in the combination polymers is freely selectable.

In an alternative, the combination polymers comprise at least one monomer selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and/or SEQ ID NO: 11 and the homologs and parts or fragments thereof, and at least one peptide binding to Abeta monomers or to Abeta oligomers or Abeta fibrils, which is different from the monomers selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and/or SEQ ID NO: 11 and/or the homologs thereof and parts or fragments thereof, as a further monomer.

Polymers can be produced by chemical synthesis or peptide synthesis, for example.

In one embodiment of the invention, the monomers are covalently bonded to each other. In another embodiment of the invention, the monomers are not covalently bonded to each other.

A covalent bond or coupling of the monomer units within the meaning of the invention is present if the peptides are linearly coupled to each other head to head, tail to tail, or head to tail, without linkers or linker groups being used in between.

A non-covalent bond within the meaning of the invention exists if the monomers are coupled to each other via biotin and streptavidin, in particular streptavidin tetramer.

In one variant of the present invention, the monomers can be linearly coupled to each other, in particular as described above. In another variant, the monomers are coupled to each other in a branched manner to obtain the polymer according to the invention.

According to the invention, the branched polymer can be a dendrimer in which the monomers are covalently or not covalently coupled to each other.

Alternatively, the monomers can also be coupled to a platform molecule (such as PEG or sugar) and thus form a branched polymer.

Alternatively, combinations of these options are also possible.

The polymers having the composition according to the invention, which are composed of peptides according to the invention that, in turn, bind to Abeta monomer or Abeta oligomer or Abeta fibrils, advantageously exhibit synergistic effects in terms of the selectivity and affinity thereof to the Abeta monomers with respect to the individual peptides. In other words, the polymers according to the invention are superior to the individual peptides of which they are composed. Synergistic effects within the meaning of the present invention are effects that exhibit a higher selectivity or specificity and/or affinity with respect to the Abeta monomer or Abeta oligomer or Abeta fibrils, in particular the $K_D$ value regarding the bond to Abeta monomer or Abeta oligomer or Abeta fibrils compared to the individual peptide units.

In a further particularly advantageous embodiment of the invention, the polymers, and more particularly the dimers, (in vitro or in vivo) advantageously act more efficiently than the individual peptide units in the animal model experiment.

In one variant of the invention, peptides or polymers are used which bind to an Abeta monomer or Abeta oligomer or to Abeta fibrils with a dissociation constant ($K_D$ value) of no more than 500 µM, preferably 250, 100, 50 µM, particularly preferably 25, 10, 1 µM, particularly preferably with a dissociation constant ($K_D$ value) of no more than 500 nM, 250, 100, 50, particularly preferably 25, 10, 1 nM, 500 µM, 100, 50, 25, 20, 15, 10, 9, 8, 7, 6, 5, 4, 3, 2, 1 µM to sub-ρM, wherein any intermediate value is possible.

In one embodiment of the invention, the affinity is defined by way of the dissociation constant ($K_D$ value). In one embodiment of the invention, the dissociation constant ($K_D$ value) of the peptide according to the invention is reduced. This is, a higher binding affinity and higher effectiveness of the decomposition and/or of the prevention of the formation of toxic amyloid beta oligomers. This applies in particular, but not exclusively, to a lower $K_D$ value at the high-affinity site of the Abeta monomer or Abeta oligomer.

Fragments and parts advantageously exhibit a similar or identical effect as the peptides according to the invention.

Monomers and polymers are hereinafter referred to as peptides according to the invention.

In one embodiment of the invention, the peptides according to the invention are provided with an acid amide group at the free C-terminus. The peptides according to the invention, for example the peptides according to SEQ ID NOS: 1-11, are then amidated at position 12 at the free C-terminus. Dimers therefrom are amidated at position 24 at the free C-terminus, and so forth.

In a further embodiment of the invention, the peptides according to the invention, and in particular the peptides according to SEQ ID NOS: 1-11 are covalently bonded to each other at the free C-terminus, with the free N-terminus, and are then present in corresponding cyclized form. The ring closure also advantageously causes the carboxyl group at the free C-terminus to no longer be present.

The peptide according to the invention advantageously comprises an amino acid sequence in which the cyclization of the linear molecule has been carried out, for example, by way of a covalent bond of the first amino acid with the last amino acid, such as by way of a condensation reaction. Other options for cyclization exist, of course, for example by coupling other amino acids to each other. The coupling of the second amino acid to the last amino acid shall only be mentioned by way of example. Any possible other coupling is equally conceivable.

If the first and last amino acids of the peptide are coupled to each other, this advantageously results in no open ends being present in the peptide chain (amino acid sequence).

A further result of this measure is that all peptides having linear amino acid sequences that, after cyclization, yield the same, no longer distinguishable amino acid order, are identical in this regard.

Example: The linear amino acid sequence of the known peptide D3 is rprtrlhthrnr. The corresponding cyclized peptide "cD3" linked between the N-terminal amino group and the C-terminal carboxyl group by an amide bond is no longer distinguishable from the cyclized peptides prtrlhthrnrr, rtrlhthrnrrp, trlhthrnrrpr, rlhthrnrrprt, lhthrnrrprtr, hthrnrrprtrl, thrnrrprtrlh, hrnrrprtrlht, rnrrprtrlhth, nrrprtrlhthr, or rrprtrlhthrn. It is still possible to derive the cD3 from each of these sequences.

The effects claimed according to the invention of higher affinity, specificity and effectiveness moreover occur with respect to one, preferably even with respect to each, linear binding peptide from which a cyclized or otherwise modified peptide according to the invention can be derived.

Otherwise, the production of cyclized peptides is state of the art and can be carried out, for example, according to the method as described in DE 102005049537 A1.

The cyclization via the first and last amino acids of the peptide advantageously also means that there are no longer any "open" ends of the peptide chain, which often represent points of attack for peptide-decomposing activities in cells, animals or humans, such as by way of aminopeptidases and carboxypeptidases.

Using cyclized peptides according to the invention, such as ANK6 according to SEQ ID NO: 1, furthermore advantageously achieves that, as a side effect, these cyclized peptides or polymers according to the invention are also potentially not easily decomposed, although this effect is not decisive. Incidentally, as was shown, this effect also applies only for the case of a head-to-tail or tail-to-head cyclization, in which the two ends of the linear peptide are correspondingly coupled to each other.

One variant of the invention relates to a peptide including the amino acid sequence according to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and/or SEQ ID NO: 11 and/or homologs thereof having an identity of at least 50%.

Within the meaning of the invention, "homologous sequences" or "homologs" shall mean that an amino acid sequence has an identity of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 with one of the above-mentioned amino acid sequences of the monomers. Instead of the term "identity," the terms "homologous" or "homology" are used as synonyms in the present description. The identity between two nucleic acid sequences or polypeptide sequences is calculated by comparison with the aid of the BESTFIT program, based on the algorithm by Smith, T. F. and Waterman, M. S (Adv. Appl. Math. 2: 482-489 (1981)), setting the following parameters for amino acids: Gap creation penalty: 8 and Gap extension penalty: 2; and setting the following parameters for nucleic acids: Gap creation penalty: 50 and Gap extension penalty: 3. The identity between two nucleic acid sequences or polypeptide sequences is preferably defined by the identity of the nucleic acid sequence/polypeptide sequence over the entire respective sequence length, as it is calculated by comparison with the aid of the GAP program, based on the algorithm by Needleman, S. B. and Wunsch, C. D. (J. Mol. Biol. 48: 443-453), setting the following parameters for amino acids: Gap creation penalty: 8 and Gap extension penalty: 2; and setting the following parameters for nucleic acids: Gap creation penalty: 50 and Gap extension penalty: 3.

Two amino acid sequences are identical within the meaning of the present invention if they have the same amino acid sequence.

In one variant, homologs shall be understood to mean the corresponding retro-inverse sequences of the above-mentioned monomers. According to the invention, the term "retro-inverse sequence" denotes an amino acid sequence that is composed of amino acids in the enantiomeric form (inverse: chirality of the alpha carbon atom is inverted), and in which additionally the sequence order was reversed compared to the original amino acid sequence (retro=reverse).

In a further variant, the peptides according to the invention bind to parts of the amyloid beta peptide.

In a further variant, the peptides according to the invention have sequences that differ from the indicated sequences by up to three amino acids.

Moreover, peptides containing the above-mentioned sequences are also used as sequences.

In a further variant, the peptides comprise fragments of the above-mentioned sequences or comprise homologous sequences with respect to the above-mentioned sequences.

According to the invention, the peptide is a peptide for use in medicine, and preferably for treating or diagnosing Alzheimer's disease.

In one embodiment of the present invention, the peptide is substantially composed of D-amino acids.

Within the meaning of the present invention, the expression "substantially composed of D amino acids" shall mean that at least 50%, 55%, 60%, 65%, 70%, preferably 75%, 80%, particularly preferably 85%, 90%, 95%, and in particular 96%, 97%, 98%, 99% or 100% of the monomers to be used according to the invention are composed of D amino acids.

In one embodiment of the present invention, the peptides according to the invention are derivatives of the D-enantiomeric D-peptide D3. Derivatives within the meaning of the invention are peptide sequences that are derived from D3 and are obtained according to one of the three following methods:

a) changing the order and/or number of the amino acid building blocks in D3. Only amino acids that are present in the D3 sequence are used.

b) deleting 1, 2, 3, 4, 5, 6, 7, 8, 9, 10 or 11 amino acids of the D3 sequence.

c) exchanging 1, 2, 3, 4, 5 or 6 amino acids with other amino acids, preferably D-enantiomers.

A further variant concerns a peptide according to the invention for inhibiting the fibril formation of amyloid beta peptides. The peptides and/or polymers according to the invention detoxify the Abeta oligomers or polymers formed thereof, and fibrils, for example by binding to Abeta monomers, thus converting them into non-toxic compounds. The present invention thus also relates to a method for detoxifying Abeta oligomers, and the polymers or fibrils formed thereof.

In one embodiment, the invention also relates to peptides according to the invention that are linked to another substance.

The linkage within the meaning of the invention is a chemical bond as it is defined in Römpp Chemie Lexikon (chemistry encyclopedia), 9th edition, volume 1, page 650 et seq., Georg Thieme Verlag, Stuttgart, preferably a principal valence bond, and more particularly a covalent bond.

The substances, in one variant, are pharmaceutical products or active ingredients, defined according to German Drug Act § 2 or § 4 (19), as amended in September 2012. In one alternative, active ingredients are therapeutically active substances that are used as active pharmaceutical substances. Preferably anti-inflammatory agents are used.

In a further variant, the substances are compounds that enhance the effect of the peptides.

In one alternative, such compounds are aminopyrazole and/or aminopyrazole derivatives. Aminopyrazole derivatives within the meaning of the invention are 3-aminopyrazole-5-carboxylic acid or 3-nitropyrazole-5-carboxylic acid and all derivatives in which the heterocyclic CH group was replaced with —CR— or —N— or —O— or —S—, and all peptidic dimers, trimers or tetramers derived therefrom, preferably aminopyrazole trimer.

In a further alternative, they are compounds that improve the solubility of the peptides and/or passage of the blood brain barrier.

In one alternative, the peptides according to the invention have any arbitrary combination of at least two or more features of the above-described variants, embodiments and/or alternatives.

Within the scope of the invention, it was furthermore found that amidated and/or cyclized peptides have a higher binding affinity to Abeta monomer, than linear binding peptides in which the free C-terminus, which is to say the C-terminal carboxyl group, is not modified and correspondingly has a negative charge. This means that the $K_D$ value is lower in the modified peptides than in linear peptides in which the free C-terminus, which is to say the C-terminal carboxyl group, is not modified and correspondingly has a negative charge.

In a further preferred embodiment of the invention, the binding affinity of the peptides modified according to the invention having no negative charge at the C-terminus, compared to linear peptides having a negative charge at the C-terminus, but otherwise having the same amino acid sequence, is thus increased by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, in particular 100%, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, in particular 200%, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, in particular 300%, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, in particular 400%, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, advantageously even 500%, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572 573, 574, 575, 576, 577, 578, 579, 580, 581, 582, 583, 584, 585, 586, 587, 588, 589, 590, 591, 592, 593, 594, 595, 596, 597, 598, 599, particularly advantageously 600%, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670 671, 672, 673, 674, 675, 676, 677, 678, 679, 680, 681, 682, 683, 684, 685, 686 687 688, 689, 690, 691, 692, 693, 694, 695, 696, 697, 698, 699, particularly advantageously 700%, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, likewise particularly advantageously 800%, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, likewise particularly advantageously 900%, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or even by 1000%, or even by 10000% or even by up to 100000% or 1000000%, wherein any intermediate value is possible. This applies in particular to the higher affinity to the high-affinity site of the Abeta monomer or Abeta oligomer.

This is indicated by a correspondingly reduced $K_D$ value. Compared to a linear, binding peptide having a negative charge at the C-terminus, the $K_D$ value, as a measure of the binding affinity of a modified, and in particular cyclized, peptide to amyloid beta monomer or to Abeta oligomer, is reduced by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, in particular 99.1, 99.2, 99.3, 99.4, 99.5%, 99.6, 99.7, 99.8, 99.9 to 99.99, or even 99.999%, wherein any intermediate value is possible.

Advantageously, these lower $K_D$ values refer in particular, but not exclusively, to the high-affinity site of Abeta monomer or Abeta oligomer.

The modified peptides can then be used more efficiently as probes for diagnostic purposes than linear, binding peptides having a negative charge at the free C-terminus, in particular more efficiently than the linear peptide analogs thereof having an identical amino acid sequence.

However, they can, in particular, also be used more efficiently as therapeutic agents than linear binding peptides having a negative charge at the free C-terminus, and in particular more efficiently than the linear peptide analogs thereof having an identical amino acid sequence.

It was furthermore found within the scope of the invention that peptides thus modified prevent the formation of particularly toxic amyloid beta oligomers, or cause the destruction and/or final detoxification thereof, with higher effectiveness or efficiency than peptides having a negative charge at the free C-terminus, in particular than the peptide analogs thereof having an identical amino acid sequence. This effectiveness is in particular increased by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9, and particularly advantageously even by 100%.

In a particularly preferred embodiment of the invention, the effects of increased affinity with respect to Abeta monomer or Abeta oligomer or Abeta fibrils, and the associated simultaneous effectiveness of elimination, and final detoxification (or formation) of Abeta oligomers also take place in vitro and/or in vivo.

The invention further relates to a peptide according to the invention for binding to aggregated Abeta peptides.

The invention moreover relates to a method for producing the peptide according to the invention by way of peptide synthesis, as known to a person skilled in the art, for example, organic synthesis methods for arbitrary low-molecular-weight compounds and/or mutagenesis and recombinant production.

The invention also relates to a composition containing the peptides according to the invention, in particular for treating and diagnosing Alzheimer's disease.

The present invention further relates to a composition containing the peptides according to the invention, in particular for preventing toxic Abeta oligomers, or for destroying polymers or fibrils formed thereof.

The "composition" according to the invention can be a vaccine, a drug (such as in tablet form), an injection solution, a food or dietary supplement, for example, containing the peptides according to the invention in a formulation to be produced based on expert knowledge.

The invention further relates to a KIT containing the peptides according to the invention.

In such a KIT, the peptides according to the invention can be packaged in containers, optionally with/in buffers or solutions. All components of the KIT may be packaged in the same container or separately from each other. The KIT can moreover include instructions for the use thereof. Such a KIT can include, for example, the peptides according to the invention in an injection vial having a stopper and/or septum. A disposable syringe can also be included therein, for example.

The present invention further relates to the use of the peptide according to the invention as a probe for identifying and qualitatively and/or quantitatively determining amyloid beta monomers, amyloid beta oligomers or Abeta fibrils.

The present invention further relates to a probe, containing the peptides according to the invention for identifying and qualitatively and/or quantitatively determining amyloid beta monomers or amyloid beta oligomers.

Such probes are of great importance in enabling early diagnosis of Alzheimer's disease. Early diagnosis allows the disease to be counteracted at a very early stage.

Such molecular probes contain the polymers according to the invention and optionally dyes, fluorescent dyes, radioactive isotopes (PET and the like), gadolinium (MRI), and alternative substances suitable for the imaging of probes and can be injected in the patient, for example intravenously. After passing the blood-brain barrier, the probes can bind to Abeta monomers, Abeta oligomers and/or plaque. The Abeta oligomers and/or plaque thus marked can be rendered visible using imaging processes, such as SPECT, PET, CT, MRI, proton MR spectroscopy and so forth.

The invention further relates to the use of the peptide for preventing amyloid beta oligomers and/or amyloid beta peptide aggregates and/or amyloid beta fibrils.

The peptide according to the invention is also used to detoxify toxic amyloid beta oligomers and/or aggregates. It is used in particular to bind to amyloid beta oligomers and/or aggregates and thus form amorphous, non-toxic aggregates.

It was found that, when Aβ oligomers are already present, the goal of a treatment must be to address these with substances that have the highest possible affinity to Abeta monomer. De facto, the affinity with respect to Abeta monomer cannot be too high, and the corresponding dissociation constant of the peptide according to the invention is then in the sub-ρM range or ρM range or even lower.

It was found within the scope of the invention that Abeta monomers, as building blocks of the Abeta oligomers, are continuously created in the human body and presumably are not toxic per se. There is even the possibility that monomers have a positive function. Abeta monomers are able to randomly agglomerate as a function of the concentration thereof. The concentration is dependent on the formation and decomposition rate thereof in the body. If the concentration of Abeta monomers in the body rises with increasing age, spontaneous agglomeration of the monomers to form Abeta oligomers is increasingly likely. It is possible that the Abeta oligomers thus created multiply analogously to the prions and ultimately lead to Alzheimer's disease.

It was furthermore found that an important difference between preventing and treating, or even curing, Alzheimer's disease lies in the fact that prevention can potentially already be achieved by preventing the formation of the first Abeta oligomers. Just a few high-affinity Abeta monomer ligands are sufficient for this purpose, which simultaneously have low affinity and selectivity (or specificity) with respect to the Abeta oligomers.

These requirements in regard to the diagnosis (probes) and the treatment of Alzheimer's disease are met with the provision of the peptides according to the invention. The peptides according to the invention, with a view to the diagnosis and/or treatment, bind the Abeta monomers or Abeta oligomers with an accordingly low dissociation constant. The invention accordingly further relates to the use of the peptides according to the invention as a therapeutic agent for Alzheimer's disease. A high specificity for and/or affinity to the target molecule of the peptides according to the invention causes particularly strong binding of the peptides according to the invention to the target molecules. The formed complexes have a lower dissociation constant ($K_D$ value).

Using the thioflavin T assay, it was possible to show that the peptides according to the invention very efficiently inhibit the fibril formation of Abeta peptides.

The invention further relates to the use of the peptides according to the invention in a method for treating (in vitro, ex vivo) blood, blood products and/or organs, characterized in that the blood, the blood products and/or the organs are derived from the human or animal body and A (amyloid) beta oligomers are removed and/or detoxified.

The term 'binding affinity' within the meaning of the invention is the measure of the binding strength between the binding partners in the case of protein-ligand interactions, and the binding specificity with respect to Abeta monomer indicates that a bond exists only with Abeta monomers, and no bond, or only a weak bond, exists with other Abeta species. The quotient of the binding signal of Abeta monomers and Abeta oligomers, or Abeta monomers and Abeta fibrils, or equivalently for Abeta oligomers, is provided as a specific value. Specific binding means that the quotient is greater than 1.

Analogously, binding specificity with respect to Abeta oligomer means that a bond only exists with Abeta oligomers, and no bond, or only a weak bond, exists with other Abeta species. The quotient of the binding signal of Abeta oligomers and Abeta monomer, or Abeta oligomers and Abeta fibrils, or equivalently for Abeta monomers, is provided as a specific value. Specific binding again means that the quotient is greater than 1.

If Abeta oligomers are already present, the goal of a treatment should be to address these with substances that have the highest possible affinity and specificity to Abeta monomers, so as to eliminate Abeta oligomers. This is achieved by way of the peptides according to the invention.

By optimizing the already known peptide D3, the mechanism of action is to remain similar or identical, but the substances are to have more efficient properties. The properties are, among other things, a binding affinity and specificity to Abeta monomers or oligomers, the inhibition of Abeta fibril formation, the inhibition of Abeta cytotoxicity, the precipitation of Abeta oligomers, and the conversion of Abeta fibrils into non-toxic, non-amyloid species.

The optimization was achieved by exchanging 4, 5, 6 or 7 amino acids of the original D3 peptide and deletion.

D3 was optimized by using peptide microarrays. For this purpose, in a first step each amino acid of the 12-mer peptide was exchanged against 19 natural amino acids and 13 further amino acids in the D-enantiomeric form. In a second step, the most promising exchanges were combined with one another. In doing so, 4, 5, 6 or 7 amino acids of the original D3 peptide were exchanged. Furthermore, one amino acid was deleted. Since the binding of the peptide is to be directed specifically against a species of Abeta (monomers, oligomers or fibrils), the microarrays were treated with the different species and, by way of calculation, binding of other species that may be present in the incubation batch was precluded.

Eleven peptides were determined that bind specifically and with high affinity with respect to Abeta monomer. These are the peptides according to SEQ ID NOS: 1-11 denoted by ANK1-7 and ANK15-18. High affinity shall be understood to mean $K_D$ values 2 times to 10 times lower than D3.

D3 (prior art): rprtrlhthrnr a) "ANK1" (free N-terminus, amidated C-terminus): rkrirlvyhinr b) "ANK2" (free N-terminus, amidated C-terminus): rkrirl06yhinr c) "ANK3" (free N-terminus, amidated C-terminus): rkrirl06yhwnr d) "ANK4" (free N-terminus, amidated C-terminus): rkrirlvyhwnr e) "ANK5" (free N-terminus, amidated C-terminus): rkrvrlvyhkkr f) "ANK6" (free N-terminus, amidated C-terminus): rkrirlvtkkkr g) "ANK7" (free N-terminus, amidated C-terminus): rkrvrl02thikr h) "ANK15" (free N-terminus, amidated C-terminus): rprvrl06yhwnr i) "ANK16" (free N-terminus, amidated C-terminus): rkr07rlvtkrnr j) "ANK17" (free N-terminus, amidated C-terminus): rkrirl06yhikr k) "ANK18" (free N-terminus, amidated C-terminus): rpr07rlhtkkkr where 02: 4-fluorophenylalanine (D)

06: Phenylglycine (D)

07: D-Homoarginine

According to the invention, all the peptides were also used as double peptides and/or in cyclized form. The effectiveness of the peptides can thus be further increased.

By binding to Abeta monomer, the peptides ANK1-7 and ANK15-18 can be used as a drug against Alzheimer's disease. Oligomer specific peptides can additionally be used as probes for diagnosis due to the specific binding thereof to Abeta oligomers.

BRIEF DESCRIPTION OF THE DRAWINGS

The invention will be described in more detail hereafter based on exemplary embodiments and the accompanying figures, without thereby limiting the invention.

In the drawings.

DESCRIPTION OF THE PREFERRED EMBODIMENTS

For the peptide microarray using D3 derivatives, this was covalently coupled via the C-terminus on glass slides as shown hereafter.

First generation: D3 in each case with 1 exchange against 19 natural amino acids and 13 non-natural amino acids Second generation: The exchanges that cause more efficient binding of the peptides to Abeta were combined with each other.

Pretreatment of the peptide microarray slides:

briefly dip 3× in ethanol (96%) and then wash with $H_2O$ (30 minutes)

briefly dry by way of centrifuging

Preparation of monomers and oligomers:

size exclusion chromatography according to Johansson et al. 2006 (Johansson, A.-S. et al. Physiochemical characterization of the Alzheimer's disease-related peptides Aβ1-42Arctic and Aβ1-42 wt. FEBS Journal 273, 2618-2630 (2006)).

oligomers were fractionated at 8-9 ml, monomers at 16-17 ml.

Preparation of fibrils:

incubate Abeta over 3 days, centrifuge, discard supernatant and resuspend in buffer (repeat 3 times)

Carrying out the peptide microarray:

incubate with FITC Abeta monomers, oligomers, fibrils and FITC for 1 hour at room temperature wash: TBS-T briefly 3× (only TBS-T buffer is replaced), 3×10 minutes in a flacon, 3×$H_2O$, 3×10 minutes dry by way of centrifugation The binding of the fluorescence-labeled Abeta to the immobilized peptides is detected by way of the fluorescent dye using the microarray reader FLA800 from Fuji Film. The more Abeta binds to the peptide, the higher is the fluorescence signal.

carrier set mode: slides
resolution: 10 μm
scan mode: high sensitivity (slow): scan pixel at 200 mm/s
laser: 473 nm
filter: 530 DF 20
photomultiplier tube (PMT) HV (%): 100
images were stored as .tif files The software, AIDA Metrix, from Raytest was used to evaluate the fluorescence signals:

| Grid definition first level | |
|---|---|
| rows | 1 |
| columns | 1 |
| second level | |
| rows | 12 |
| columns | 4 |
| X spacing | 0 |
| Y spacing | 0 |
| 3rd level | |
| rows | 9 |
| columns | 9 |
| diameter | 80 μm |
| background definition | |
| local dot rings | |
| inflate dots | 150 μm |
| ring width | 30 μm |
| by area | mean |
| alignment defaults (parameter) | |
| diameter | 100% |
| mobility | restricted align grid, align dots |
| alignment defaults (process) | |
| bkg deviation threshold | 2.0*StdDev |

To ensure the reproducibility of the results, the incubation of the peptide microarrays is carried out at least three times for each species.

The measured fluorescence signals of the reproductions are standardized using a median-based standardization, and the control was subtracted from the signal. This avoided the binding of the fluorescence-labeled Abeta via the dye.

The binding signals of an Abeta species to a peptide were averaged.

So as to determine the binding specificity, the quotient of the species to which the peptide is to specifically bind and another species is created.

Example: binding specificity of peptide X to Abeta monomers=binding signal of peptides X to monomers/binding signal of peptides X to oligomers.

The peptides according to the invention ANK1-7 and ANK15-18 result in inhibition of Abeta fibrillization, inhibition of the Abeta cell toxicity, elimination of Abeta oligomers, and conversion of Abeta fibrils into non-toxic, non-amyloid species. There is binding affinity and specificity for Abeta monomers.

The binding affinity is the measure for the binding strength between the binding partners in the case of protein-ligand interactions, and the binding specificity indicates that a bond exists only with Abeta monomers, and no bond, or only a weak bond, exists with other Abeta species. Here, the quotient of the binding signal of Abeta monomers and Abeta oligomers, or Abeta monomers and Abeta fibrils, or equivalently for Abeta oligomers, is provided as a specific value. Specific binding means that the quotient is greater than 1.

Specifically, the following data was determined:

| | Binding signal to Abeta monomers | Binding signal to Abeta oligomers | Binding signal to Abeta fibrils | Binding specificity monomer to oligomer | Binding specificity monomer to fibrils |
|---|---|---|---|---|---|
| ANK1 | 6.6 | 1.9 | 1.3 | 3.5 | 5.1 |
| ANK2 | 5.6 | 1.6 | 0.8 | 3.4 | 7.1 |
| ANK3 | 3.6 | 0.6 | 0.2 | 6.5 | 21.9 |
| ANK4 | 4.4 | 1.3 | 1.0 | 3.3 | 4.3 |
| ANK5 | 4.3 | 0.7 | 2.0 | 5.9 | 2.2 |
| ANK6 | 4.9 | 1.2 | 2.5 | 4.1 | 1.9 |
| ANK7 | 2.1 | 0.3 | 0.3 | 6.4 | 6.8 |
| ANK15 | 1.3 | 0.6 | 0.1 | 2.2 | 12.2 |
| ANK16 | 11.9 | 1.4 | 1.5 | 8.6 | 8.1 |
| ANK17 | 4.7 | 1.0 | 1.9 | 4.8 | 2.5 |
| ANK18 | 1.2 | 0.2 | 0.1 | 7.0 | 9.4 |
| D3 | 0.5 | 0.6 | 0.8 | 0.8 | 0.6 |

Figure 1A:
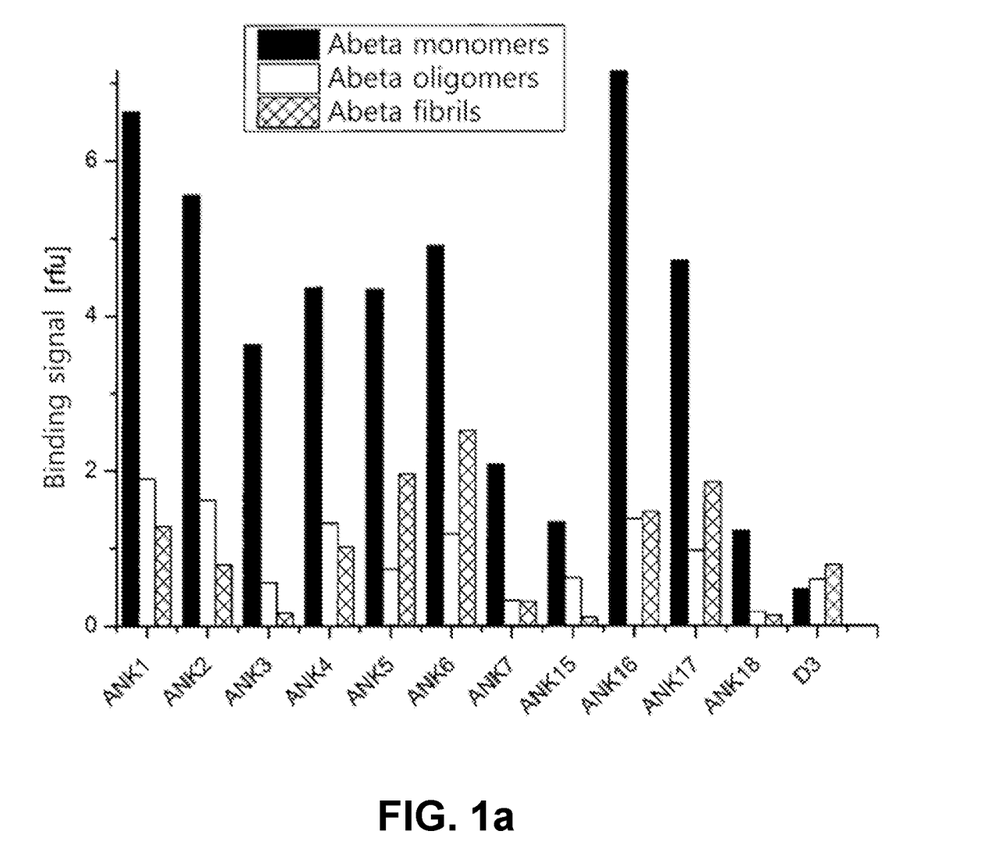
FIG. 1a shows binding signals of the peptides according to the invention to Abeta monomers, Abeta oligomers and Abeta fibrils.

FIG. 1a shows the binding signals for ANK1-ANK7 and ANK15-18, compared to D3, to Abeta monomers, oligomers and fibrils. The peptides bind to Abeta monomers significantly more efficiently than to Abeta oligomers and Abeta fibrils, which is apparent from a clear difference in the binding signal. A clear difference means at least a difference of 1.5 rfu between the binding signal of Abeta monomers and Abeta oligomers and/or Abeta fibrils.

Figure 1B:
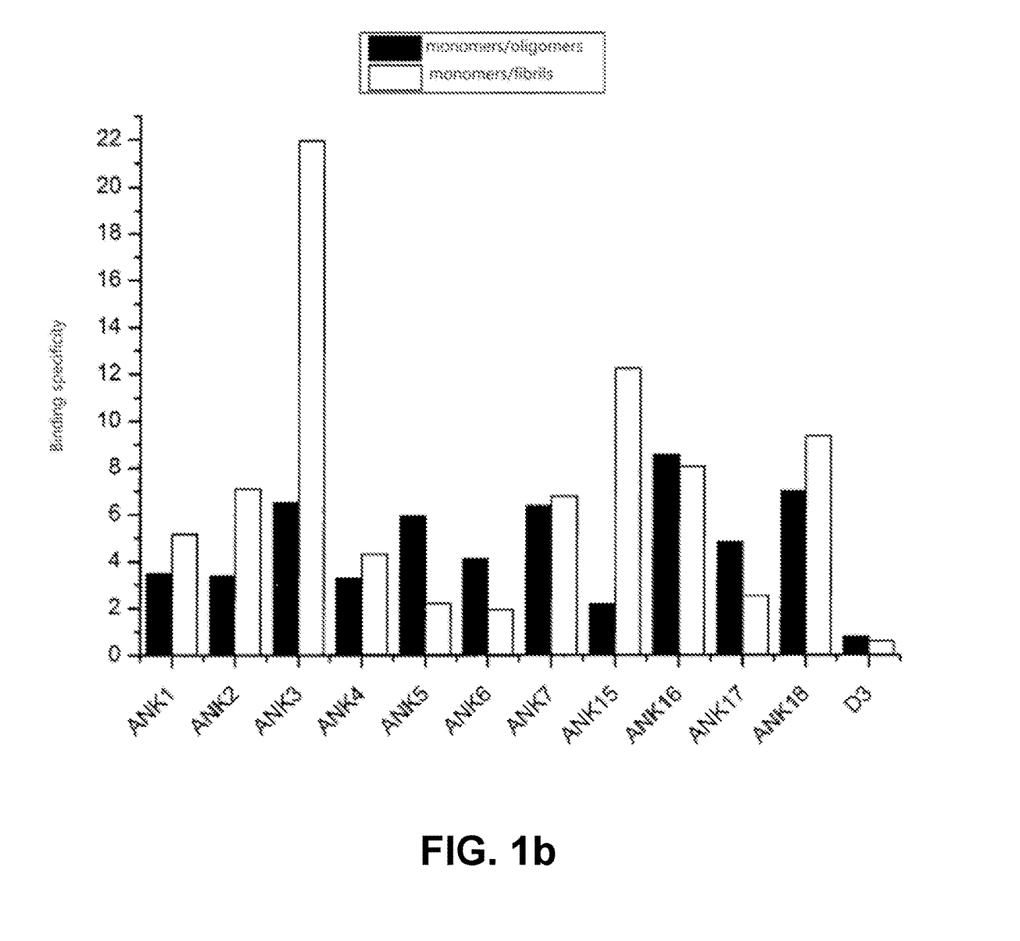
FIG. 1b shows binding specificity of the peptides according to the invention.

FIG. 1b shows the binding specificity for ANK1-7 and ANK15-18. It is apparent that the binding specificity of all peptides according to the invention with respect to Abeta monomer is greater than 1. In contrast, D3 has a binding specificity with respect to Abeta monomer of less than 1.

Using the QIAD method for the quantitative characterization of amyloid peptides and/or proteins in a sample, it was possible to quantify the properties of the substances. Pre-incubated Abeta was co-incubated with the peptides. The different Abeta species were separated by way of density gradient centrifugation and quantified in the individual fractions by way of RP-HPLC Abeta. The elimination of the Abeta oligomers in fractions 4-6 was analyzed.

Figure 2:
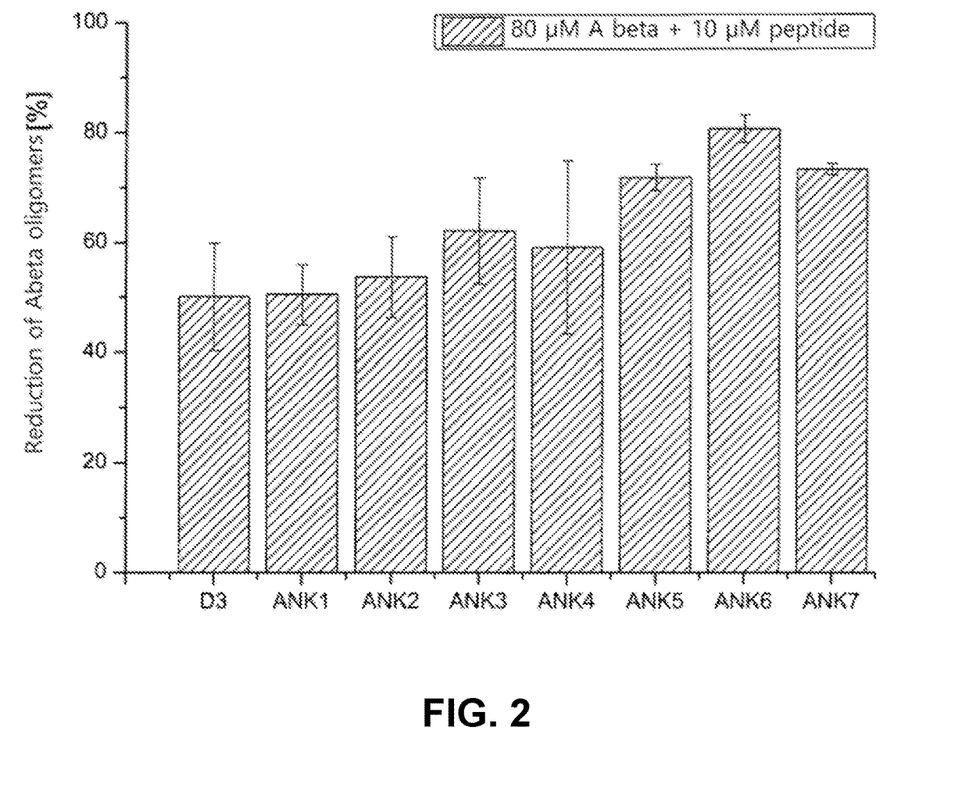
FIG. 2 shows reduction of amyloid beta oligomers by way of the peptides according to the invention.

It is shown that, in particular, ANK5, ANK6 and ANK7 eliminate Abeta oligomers more efficiently than D3, see FIG. 2. The specific binding to monomers is able to prevent the formation of oligomers, without resulting in a reduction in the concentration of Abeta monomer, and additionally, Abeta oligomers that have already developed can be removed from the dynamic balance of the different aggregate species, in keeping with Le Chatelier's principle, by way of a treatment with an Abeta monomer-stabilizing active substance, and in this way can cause Abeta oligomers to be decomposed to yield Abeta monomers.

Figure 3A:
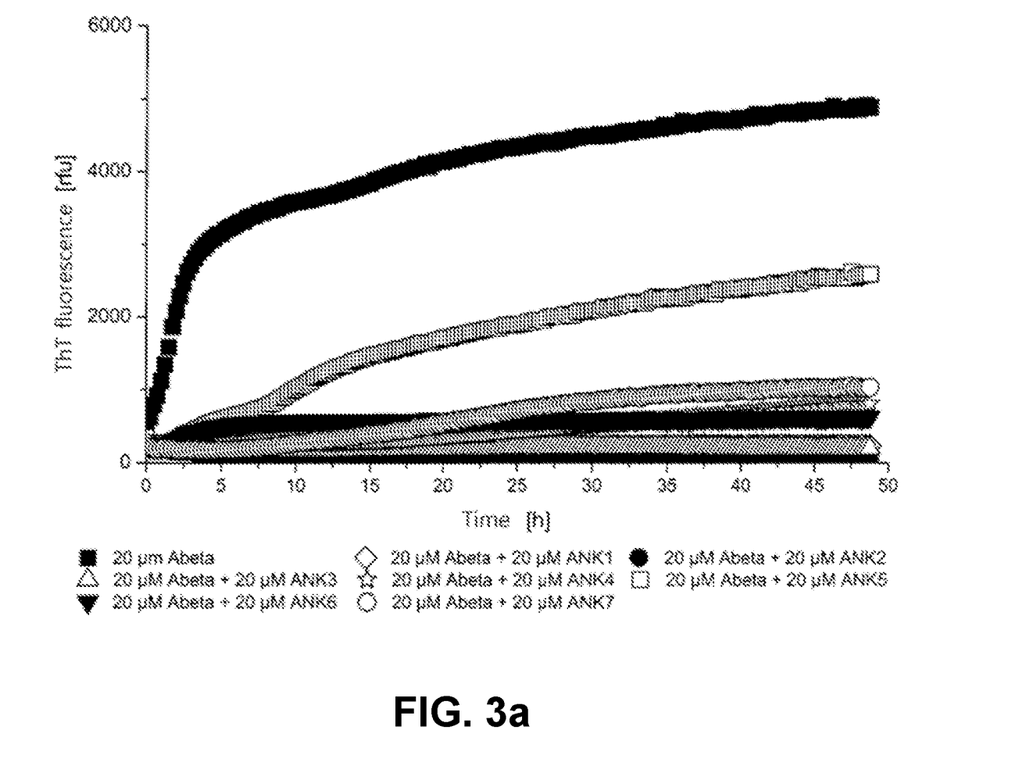
FIG. 3a shows a ThT assay of peptides according to the invention.
Figure 3B:
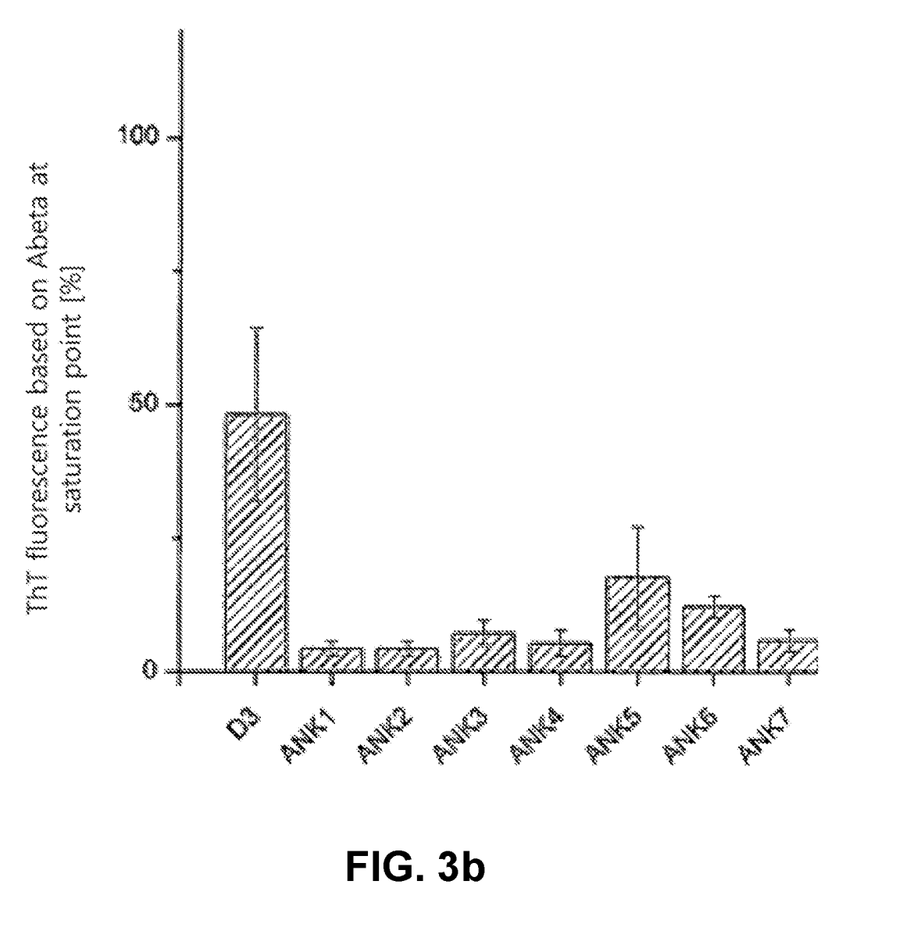
FIG. 3b shows an evaluation of a ThT assay with ThT fluorescence based on amyloid beta at the saturation point.

The ThT assay shows a clear reduction in the ThT positive Abeta fibrils after co-incubation with the tested substances (FIGS. 3a and 3b). This indicates that the aggregation is being inhibited or amorphous aggregates are being formed.

Figure 4A:
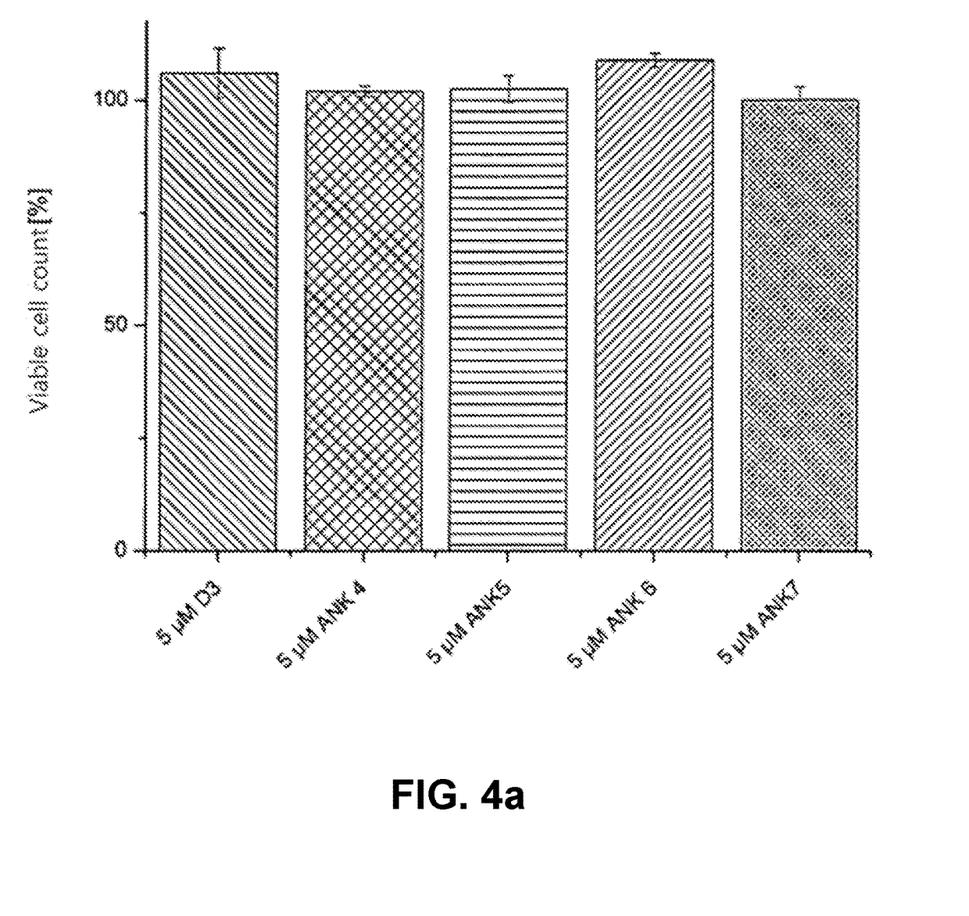
FIG. 4a shows an MTT assay on SH-SY5 cells without Abeta co-incubation.
Figure 4B:
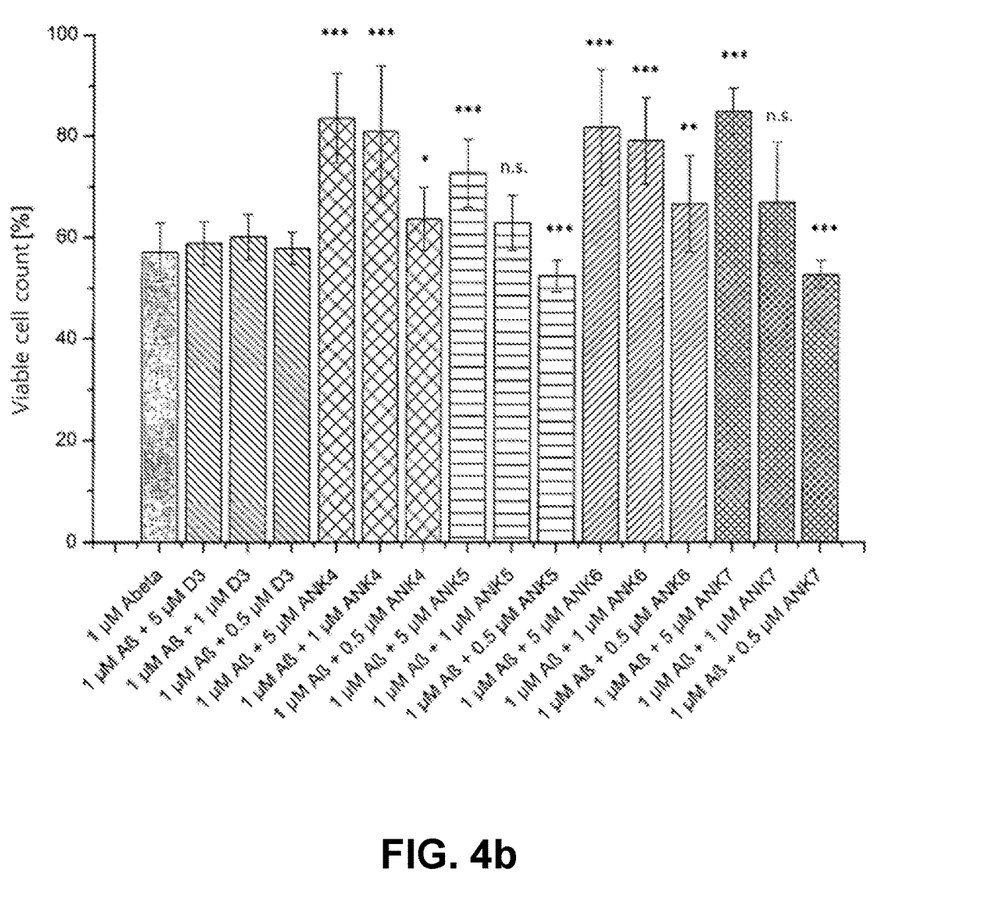
FIG. 4b shows an MTT assay on SH-SY5 cells with Abeta co-incubation.

No noteworthy toxicity of the peptides according to the invention in therapeutically relevant concentrations was established in the MTT assay on SH-SY5Y cells known to a person skilled in the art (FIG. 4). In contrast, it was possible to show that the toxicity caused by Abeta is reduced by the substances ANK4, ANK5, ANK6 and ANK7. Based on current knowledge, Abeta oligomer is the toxic species. Since the Abeta oligomers are eliminated by using the peptides, Abeta-induced toxicity is also reduced.

Specifically:

FIG. 2 shows that, at a ratio of Abeta to peptide of 8:1, the peptides ANK5, ANK6 and ANK7 reduce Abeta oligomers significantly more efficiently than D3. At this concentration, the efficiency of the other peptides is comparable to that of D3. D3 eliminates the Abeta oligomers by 50±10%, ANK1 by 51±6%, ANK2 by 54±7%, ANK3 by 62±10%, ANK4 by 59±16%, ANK5 by 72±2%, ANK6 by 81±3%, and ANK7 by 73±1%.

Compared to D3, peptides according to the invention show a reduction in Abeta oligomers that is increased by a factor of up to 1.6.

FIG. 3 shows that ANK1-7 considerably reduce the formation of ThT positive Abeta fibrils. During the entire measuring time period (48 hours), the ThT fluorescence remains at the level of the first measured value for the peptides ANK1, ANK2 and ANK3, while a slight increase is apparent for the peptides ANK4, ANK6 and ANK7 (corresponds to 13 to 21% of the ThT fluorescence of Abeta after 48 hours), and an increase to 1029 rfu is apparent for ANK5, which corresponds to 53% of the ThT fluorescence of the Abeta control after 48 hours.

FIG. 4a shows that ANK4, ANK5, ANK6 and ANK7 alone do not have a toxic effect on the cells. By co-incubating Abeta with ANK4, ANK5, ANK6 and ANK7 in various concentrations, a reduction in the Abeta toxicity was achieved, see FIG. 4b. This reduction is more efficient with the substances ANK4 and ANK6 than with D3. The significances are based on the respective concentration with D3 (* p≤0.05;  p≤0.01; * p≤0.001; n. s. not significant).

The invention claimed is:

1. A peptide binding specifically to amyloid beta species, containing at least one amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11.

2. The peptide of claim 1 for use in medicine.

3. The peptide of claim 1 for treating Alzheimer's disease.

4. The peptide of claim 1 for diagnosing Alzheimer's disease.

5. The peptide of claim 1 substantially composed of D-amino acids.

6. The peptide of claim 1 for inhibiting the formation of Abeta fibrils.

7. The peptide of claim 1 for binding to aggregated amyloid beta species.

8. A KIT, including a peptide according to claim 1.

9. A composition comprising a peptide according to claim 1.

10. A probe for specifically identifying and quantitatively and/or qualitatively determining amyloid beta monomers, amyloid beta fibrils and/or amyloid beta oligomers, comprising the peptide according to claim 1.

* * * * *